(12) United States Patent
Qureshi

(10) Patent No.: US 11,931,485 B2
(45) Date of Patent: Mar. 19, 2024

(54) IMPLANTABLE SUSTAINED RELEASE DEVICE AND A METHOD OF USE THEREFOR IN THE TREATMENT OF BRAIN DISORDERS

(71) Applicant: Adnan I. Qureshi, Columbia, MO (US)

(72) Inventor: Adnan I. Qureshi, Columbia, MO (US)

( * ) Notice: Subject to any disclaimer, the term of this patent is extended or adjusted under 35 U.S.C. 154(b) by 203 days.

(21) Appl. No.: 17/196,953

(22) Filed: Mar. 9, 2021

(65) Prior Publication Data

US 2021/0196864 A1 Jul. 1, 2021

Related U.S. Application Data

(60) Provisional application No. 63/136,811, filed on Jan. 13, 2021.

(51) Int. Cl.
| | | |
|---|---|---|
| *A61L 31/16* | (2006.01) | |
| *A61K 31/167* | (2006.01) | |
| *A61K 31/445* | (2006.01) | |
| *A61L 31/14* | (2006.01) | |

(52) U.S. Cl.
CPC ............ *A61L 31/16* (2013.01); *A61K 31/167* (2013.01); *A61K 31/445* (2013.01); *A61L 31/148* (2013.01); *A61L 2300/402* (2013.01)

(58) Field of Classification Search
None
See application file for complete search history.

(56) References Cited

U.S. PATENT DOCUMENTS

| | | | | |
|---|---|---|---|---|
| 2006/0271165 A1* | 11/2006 | Yip | ......... | A61F 2/915 623/1.53 |
| 2008/0009934 A1* | 1/2008 | Schneider | ........ | A61F 2/95 623/1.11 |
| 2009/0030505 A1* | 1/2009 | Kleiner | ........ | A61P 9/14 623/1.42 |
| 2011/0008408 A1* | 1/2011 | Shalev | ........ | A61P 25/00 514/626 |
| 2020/0000612 A1* | 1/2020 | Kealey | ........ | C23C 30/00 |

FOREIGN PATENT DOCUMENTS

| | | | | |
|---|---|---|---|---|
| WO | WO-9811846 A1 * | 3/1998 | ....... | A61B 17/12118 |
| WO | WO-2007028053 A2 * | 3/2007 | ........ | A61K 31/565 |

OTHER PUBLICATIONS

Qureshi et al. Journal of Neuroimaging 2018 28:79-85 (Year: 2018).*
Moradkhani et al. Artificial Cells, Nanomedicine, and Biotechnology 2018 46(2):355-360 (Year: 2018).*
Heller et al. Journal of NeuroInterventional Surgery 2011 3:340-343 (Year: 2011).*

* cited by examiner

*Primary Examiner* — Melissa S Mercier
*Assistant Examiner* — Caralynne E Helm
(74) *Attorney, Agent, or Firm* — Barry Choobin; Patent 360

(57) ABSTRACT

A biocompatible and bioresorbable implantable device that is intended to be deployed in the middle meningeal artery through intra-arterial catheters and release an anesthetic agent for a prolonged period into the branches of the middle meningeal artery to treat severe headaches including migraine and trigeminal neuralgias. The implantable device may be a mesh with multiple helical loops, fenestrated collapsible hollow shell or spheroid, or folded sheath.

10 Claims, 6 Drawing Sheets

IMPLANTABLE SUSTAINED RELEASE DEVICE AND A METHOD OF USE THEREFOR IN THE TREATMENT OF BRAIN DISORDERS

CROSS-REFERENCE TO RELATED APPLICATIONS

This application claims priority to the U.S. provisional patent application Ser. No. 63/136,811 filed on Jan. 13, 2021, which is incorporated herein by reference in its entirety.

FIELD OF INVENTION

The present invention relates to a sustained release device and a method of use thereof in the treatment of brain disorders, and more particularly, the present invention relates to an implantable sustained release device and method for the treatment of recurrent headaches and/or trigeminal neuralgias.

BACKGROUND

Recurrent headache disorders are among the most common disorders of the nervous system affecting a large population. Migraine and headache are leading causes of outpatient and emergency department visits and remain an important public health problem, particularly among women during their reproductive years. Headache can be very painful and impair a person to live a quality life. Globally, it has been estimated that around 50% of adults have certain symptoms of headache in the last year. Certain headache disorders and trigeminal neuralgias can be chronic and severely painful with moderate to severe disability. Available treatments are either ineffective or may require frequent medications. Therefore, a long-term desire is there for effective treatment of recurrent headaches and trigeminal neuralgias.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to an implantable sustained release device for the treatment of brain disorders including recurrent headaches.

It is another object of the present invention that the implantable device can be used for the treatment of trigeminal neuralgia.

It is still another object of the present invention that the implantable device can release an active pharmaceutical substance at a sustained rate over a prolonged period.

It is yet another object of the present invention that the implantable device is biocompatible and bioresorbable.

In one aspect, disclosed is an implantable sustained release device that can be implanted in a blood vessel supplying the dura mater of the brain for sustained release of an active pharmaceutical agent over a prolonged period for the treatment of brain disorders.

In one aspect, the implantable device can release an anesthetic agent over 3-6 months for the treatment of recurrent headaches and trigeminal neuralgias.

In one aspect, disclosed is an implantable device that is intended to be deployed in the middle meningeal artery through intra-arterial catheters and release anesthetic agent for a prolonged period into the branches of the middle meningeal artery for treating severe headaches including migraine and trigeminal neuralgias.

In one aspect, the implantable device may be a helix, a fenestrated collapsible hollow shell, spheroid, or a folded sheath.

In one aspect, the anesthetic agent can be lidocaine or bupivacaine.

In one aspect, the anesthetic is lidocaine in doses between 200-500 mg released over 3-6 months.

These and other objects and advantages of the embodiments herein and the summary will become readily apparent from the following detailed description taken in conjunction with the accompanying drawings

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
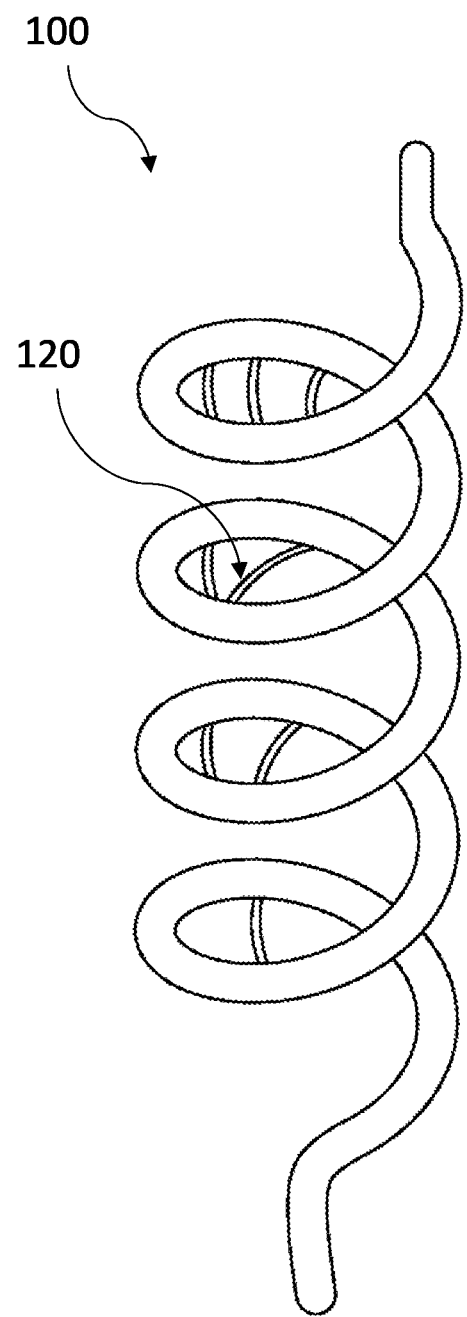
FIG. 1 shows a helical implantable sustained release device, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is an implantable sustained release device that is intended to be deployed in the blood vessels that supply the dura mater in the brain. Preferably, the disclosed device can be implanted in the middle meningeal artery for releasing an active pharmaceutical ingredient into the branches of the middle meningeal artery. The Middle meningeal artery is the predominant source of blood supply to the dura mater. The middle meningeal artery originates from the internal maxillary artery and enters the skull through the foramen spinosum of the sphenoid bone, where it then divides into anterior and posterior branches. The middle meningeal artery divides into frontal, parietooccipital, and posterior temporal branches which are approx. 400-800 μm in diameter. The middle meningeal artery is one of the main arterial supplies, although the accessory middle meningeal artery may also supply the trigeminal nerve ganglion. The artery to trigeminal nerve ganglion has been identified as a branch that arises from the extracranial segment of the middle meningeal artery before entry into the foramen spinosum.

The active pharmaceutical ingredient can be an anesthetic agent for the treatment of brain disorders such as headaches, migraine, facial pain, and trigeminal neuralgia. The device can release the anesthetic agent for a prolonged period, such as 3-6 months to treat severe headaches including migraine and trigeminal neuralgia. The anesthetic agent can be lidocaine, bupivacaine, or the like pharmacological agent. The anesthetic agent can be provided as a coating in the disclosed implantable device. The coating includes carrier polymers which provide for sustained release of the anesthetic agent. The anesthetic agent can be dispersed in a polymeric carrier and the mixture can be applied as layers on a frame of the disclosed implantable device. Multiple layers can be provided on the frame that allows sustained release of the anesthetic agent over a prolonged period. The polymeric carrier can preferably be a bioabsorbable polymer. Bioabsorbable polymers for use in medicines are known to a skilled person, and any such bioabsorbable polymers are within the scope of the present invention.

Figure 2:
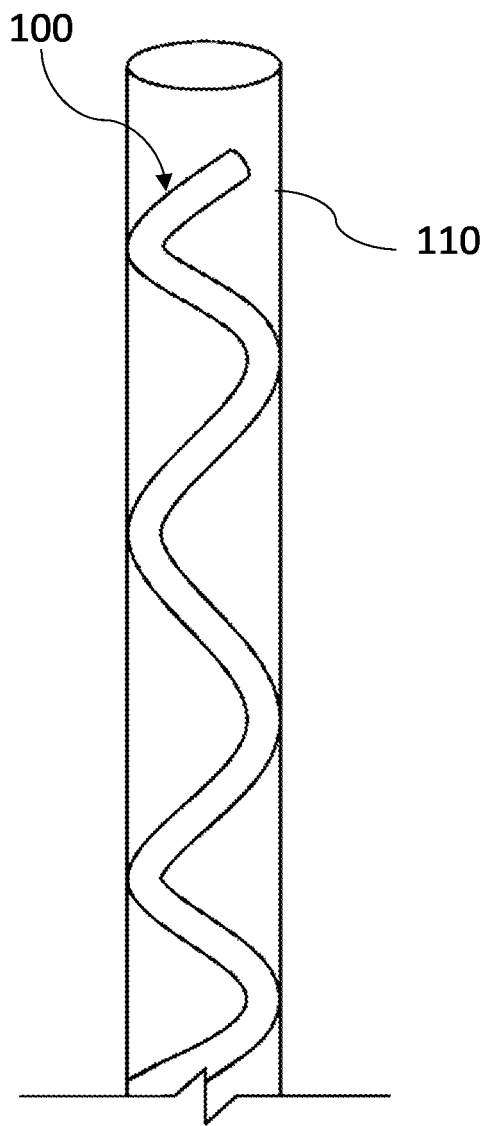
FIG. 2 shows the helical implantable sustained release of FIG. 1 in collapsed state within a catheter for implantation, according to an exemplary embodiment of the present invention.

Referring to FIG. 1, which shows an exemplary embodiment of the disclosed implantable device 100 which has a helical shape. The implantable device 100 includes a frame that can be resilient and switch between an expanded state and a collapsed state. FIG. 2 shows the implantable device 100 in the collapsed state while FIG. 1 shows the implantable device 100 in the expanded state. The disclosed implantable device can be deployed in the blood vessel using an arterial catheter 110 and the implantable device can be received in the collapsed form into the catheter.

The implantable device can be implanted into the blood vessel, such as the middle meningeal artery using an arterial catheter 110. In the middle meningeal artery, the disclosed implantable device can be deployed through an arterial route such as a femoral or radial artery. The implantable device, in the collapsed form, can be deployed in the arterial microcatheter, which can then be inserted through the artery up to the desired location i.e., the middle meningeal artery. The device can then be pushed out of the catheter with a standard microwire until the implantable device is extruded from the microcatheter into the blood vessel. The device in the blood vessel can expand and fit into the blood vessel. The implantable device by virtue of its biomechanical properties assumes the predefined shape that ensures that the implantable device remains in position in the artery without immediate displacement. In one exemplary embodiment, the diameter of the implantable device in the expanded state is no more than 2 mm.

In one exemplary embodiment, for deploying the disclosed implantable device, the procedure can be performed after arterial access is achieved by placement of a sheath in the femoral arterial or radial artery. The external carotid artery is catheterized using a 5 F or 6 F catheter. Images are obtained in anteroposterior and lateral planes and the absence of any Dural arteriovenous fistula or anastomoses between external and internal carotid artery branches can be confirmed. After confirmation, a single lumen microcatheter can be advanced over a 0.014 in. microwire through the 5 F or 6 F catheter into the external carotid artery. Under fluoroscopic guidance, the microcatheter can be advanced through the proximal internal maxillary artery and into the middle meningeal artery. A microcatheter injection can be performed in both anteroposterior and lateral planes to visualize the Dural branches of the middle meningeal artery and the absence of any contribution to ophthalmic or intracranial arteries.

Figures 3A, 3B, 3C:
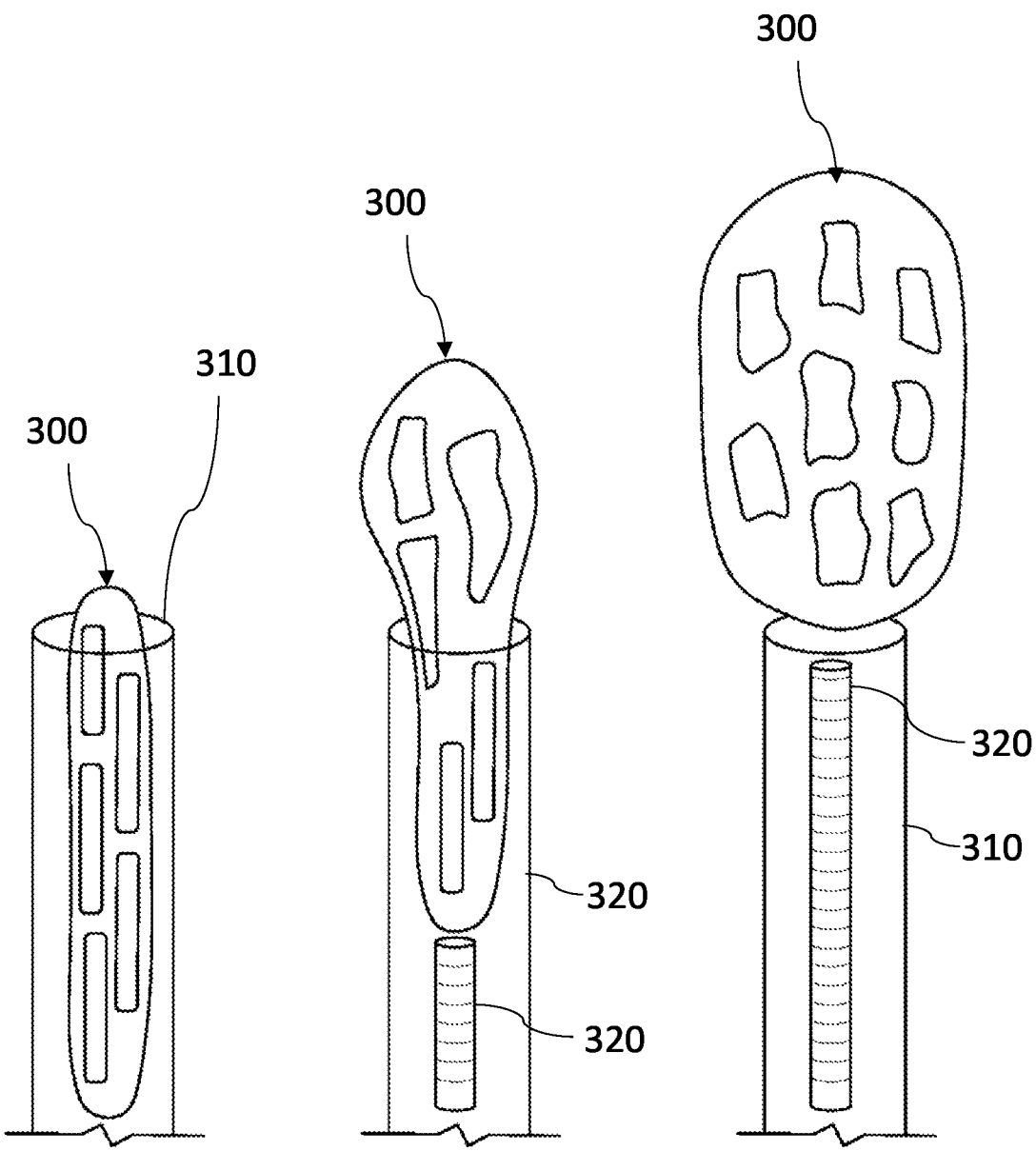
FIG. 3A shows another embodiment of the implantable sustained release device in collapsed state within a catheter for implantation, according to the present invention.
FIG. 3B shows the implantable sustained release device of FIG. 3A partially pushed out of the catheter for illustration, according to an exemplary embodiment of the present invention.
FIG. 3C shows the implantable sustained release device of FIG. 3A in the expanded state, according to an exemplary embodiment of the present invention.

The implantable device can be introduced through the exterior end of the microcatheter and pushed through the lumen using any 0.014 in. microwire. Once the implantable device reaches the distal end of the microcatheter, the device can be deployed by either pushing it forward or retracting the microcatheter with constant forward push of the delivery microwire. FIG. 3A shows another exemplary embodiment of the implantable device which is fenestrated collapsible hollow shell 300. FIG. 3A shows device 300 in collapsed state inserted in the distal end of the catheter 310. FIG. 3B shows device 300 being pushed out of the catheter 310 using a microwire 320. The portion of device 300 coming out of the catheter is being expanded. FIG. 3C shows the device 300 pushed out of the catheter 310 and expanded to the expanded state. FIG. 1 shows the helical loop-shaped device 100 in the expanded state. The frame of the device can have biomechanical properties by virtue of which the device can expand against the blood vessel and stay in place in the blood vessel.

The frame acts as a carrier for the active pharmaceutical agent, such as an anesthetic agent, that can be implanted in the blood vessel. The frame can be made from any biodegradable metal or polymer, such as magnesium alloy, polylactic acid, polycarbonate polymers, salicylic acid polymers, and/or combinations thereof. Coating of the pharmaceutically active agent can be applied directly on the frame or a base layer can be applied to the frame first.

The base layer can be of a biocompatible material that can cover the entire frame. For example, the biocompatible base layer may be made from poly(n-butyl methacrylate), poly (tetrafluoroethylene), poly(vinylidene fluoride-co-hexafluoropropylene), poly(styrene-b-isobutylene-b-styrene) Parylene C, poly(vinyl pyrrolidone), $TiO_2$ or any material that has good biocompatibility. The coating containing the active pharmaceutical agent can be coated as one or more layers on the biocompatible base layer.

Figure 4A:
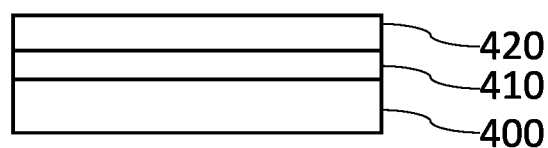
FIG. 4A shows a section of the disclosed implantable sustained release device having the frame, base layer, and a continuous layer of coating, according to an exemplary embodiment of the present invention.
Figure 4B:
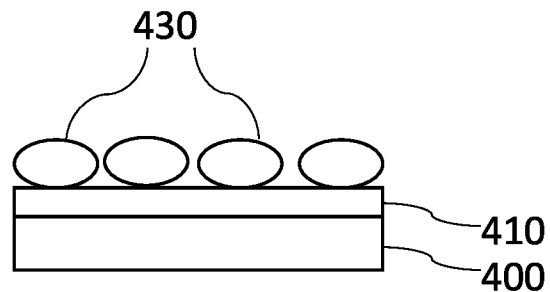
FIG. 4B shows a section of the disclosed implantable sustained release device having the frame, base layer, and a non-corrugate layer of coating, according to an exemplary embodiment of the present invention.

The coating including the active pharmaceutical agent provides for sustained release of the active pharmaceutical agent. The coating can include a bioabsorbable polymer into which the active pharmaceutical agent can be dispersed. The device can include multiple layers of the coating for sustained release. The release of the active agent depends on the total surface area of the frame. The surface area can be increased by providing elements 120 made from strands interconnecting the helical loops, shown in FIG. 1. The coating can be uniformly applied over the helical loops and the strands. Alternatively, the coating can also be applied as a layer in non-congruent portions. FIG. 4A is a sectional view of the device showing the frame 400 having the first base layer 410 and a coating 420 containing the anesthetic agent. FIG. 4B is the sectional view of the device showing the frame 400 having the uniform first base layer 410 and a coating 430 is applied as a layer of non-congruent portions.

Figure 5:
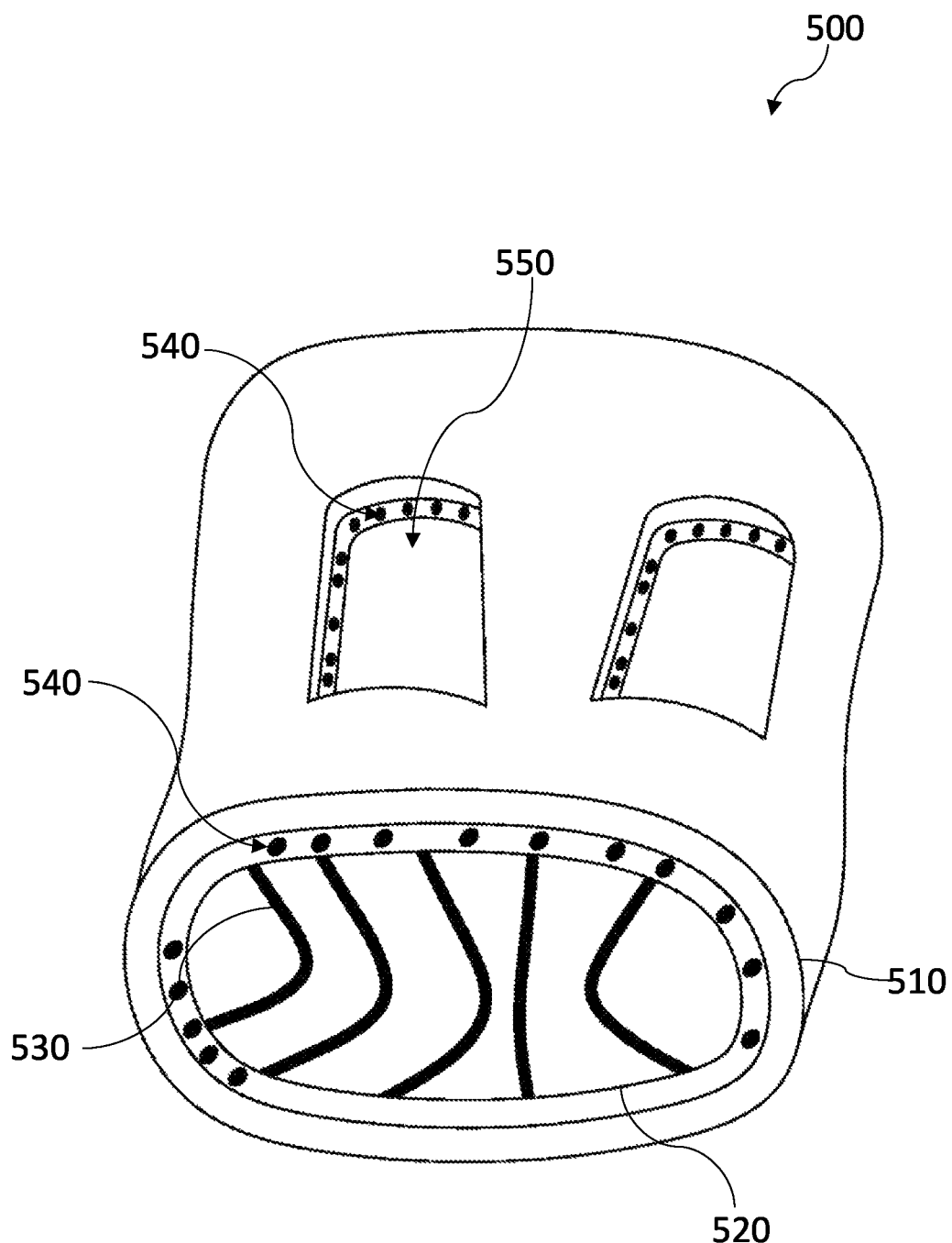
FIG. 5 shows another exemplary embodiment of the implantable sustained release device, according to the present invention.
Figure 6:
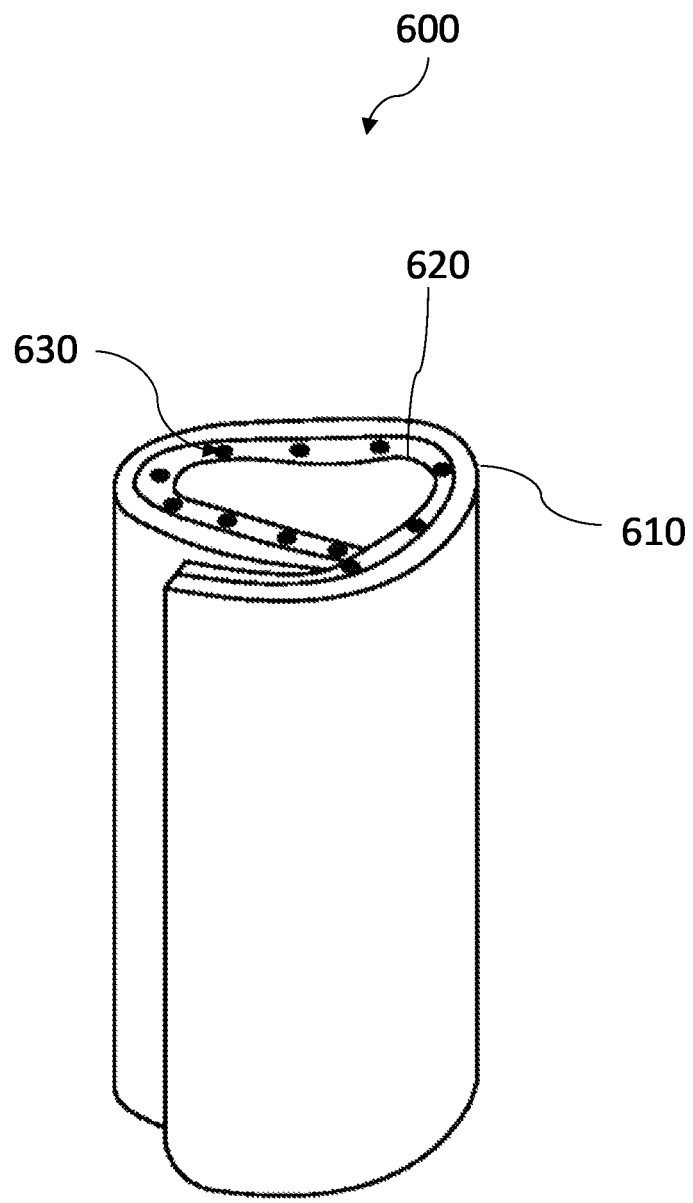
FIG. 6 shows another exemplary embodiment of the implantable sustained release device, according to the present invention.

The frame of the disclosed device can embody different geometric forms that can be collapsed under external force and expands to their shape when the external force is removed. FIG. 1 shows the device in the form of helical loops having a lumen and strands that extend across the lumen within a loop. FIG. 3C shows the disclosed device as a fenestrated collapsible hollow spheroid. FIG. 5 shows the device 500 in the form of the fenestrated collapsible hollow shell. The device 500 having a shell 510 having an inner coating 520 and mesh 530. Anesthetic agent 540 is dispersed in the coating. The shell having windows 550 for increased surface area. FIG. 6 shows the disclosed device 600 in the form of a folded sheath. The device 600 having the frame 610, a coating 620 over the frame, and an anesthetic agent 630.

Example 1

The effects of intra-arterial injection of a dose of 40 mg lidocaine and 20 mg methylprednisolone into the middle meningeal artery of two patients suffering from severe headaches were determined.

It was observed that the effect of injection of lidocaine and methylprednisolone was short-lasting with effects manifesting within 5 min and lasting 5-8 h after injection. Both patients reported improvement in headache intensity after 24 h post-procedure. Microcatheter injection was performed in both anteroposterior and lateral planes to visualize the Dural branches of the middle meningeal artery and the absence of any contribution to ophthalmic or intracranial arteries. A dose of 40 mg lidocaine (2 mg/ml dilution in normal saline) injected in 10 mg doses was administered over 5 min into the middle meningeal artery. Subsequently, 20 mg methylprednisolone (4 mg/ml dilution in normal saline) was injected over 5 min into the middle meningeal artery. Heart rate and single-lead EKG were continuously monitored, and blood pressure was monitored using an automated cuff every 3 min. The patient reported improvement in headache from a self-reported intensity of 10 (on Visual Analog scale) to 5 after 5 min of lidocaine injection. At a subsequent interview at 2.5 h post-procedure, the patient reported that headache was better than pre-procedure headache with intensity rated at 6.5. The patient reported the recurrence of headache at 8 h with intensity rated at 8. After 24 h, the patient reported an improvement in headache with intensity rated at 5. The patient appeared to be more comfortable and was discharged. On the day of discharge, the patient was resting comfortably but denied any persistent headache. The patient reported improvement in headache from a self-reported intensity of 7 (on Visual Analog scale) to 4 after 5 min of lidocaine injection. The patient reported recurrence of headache after 5 h to a self-reported intensity of 7. The patient reported complete resolution of headache after 12 h and mild headache at 16 h post-procedure.

Example 2

Trigeminal neuralgia consists of unilateral, brief/paroxysmal, or continuous pain in one or more divisions of the trigeminal nerve. The pain is secondary to hyperactivity or spontaneous impulse generation within the nerves due to extrinsic compression or intrinsic neural dysfunction. In the experiment, the intra-arterial delivery of medication for modulating trigeminal nerve ganglion function in patients with refractory trigeminal neuralgia was examined. Was administered intra-arterial lidocaine in doses up to 50 mg in the middle meningeal artery territory adjacent to the arterial branch that supplies the trigeminal nerve ganglion. Electrophysiologic monitoring was performed to serially assess the latency and amplitude of R1 and R2 responses in the blink reflex before and concurrent with each incremental dose of lidocaine. Clinical outcome assessment included a 10-point numeric rating, 4-point severity grading, and the pain-free time interval pre- and post-treatment. Intra-arterial lidocaine was administered to three patients with trigeminal neuralgia (35-year-old woman, 57-year-old man, and a 34-year-old woman). In all patients, there was a latency prolongation and amplitude reduction of R1 or R2 responses or both which was evident after 5-10 mg of lidocaine administration; a more pronounced effect was seen with increasing doses. The second and third patients reported improvement in pain severity on all scales with pain-free intervals of 5 and 3 days, respectively. There was an improvement in facial hyperalgesia in all three patients in all dermatomes. All three patient's symptoms had returned to baseline severity 1 month later. It was found that modulation of trigeminal nerve activity via the intra-arterial route is possible based on consistent intraprocedural electrophysiologic suppression and short-term clinical improvement in patients with refractory trigeminal neuralgia.

By blocking sodium channels, lidocaine stabilizes nerve membranes, delays nerve depolarization, and reduces ectopic discharges. The elimination half-life of lidocaine following an intravenous bolus injection was found to be typically 1.5-2 hours.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method of treatment of recurrent headaches and/or trigeminal neuralgia, the method comprising the steps of:
providing a sustained release device that is configured to be implanted in a blood vessel supplying the dura mater in the brain, wherein the sustained release device comprises an anesthetic agent, the sustained release device configured for sustained release of the anesthetic agent in the blood vessel for a prolonged period, wherein the sustained release device comprises a frame, wherein the frame has a helical wire shape and the helical wire shape has a lumen, wherein the frame has an expanded configuration and a collapsed configuration, wherein the frame further comprises strands that extend across the lumen within a loop;
implanting the sustained release device in the blood vessel by receiving the sustained release device in a collapsed form in an arterial microcatheter; and
releasing the collapsed sustained release device into the blood vessel by pushing out of the microcatheter with a microwire, wherein a diameter of the implantable device in the expanded state is no more than 2 mm.

2. The method according to claim 1, wherein the blood vessel is a middle meningeal artery.

3. The method according to claim 2, wherein the sustained release device in the middle meningeal artery expands such that the device maintains its position without immediate displacement.

4. The method according to claim 1, wherein the sustained release device comprises a coating on the frame and strands, the coating comprises the anesthetic agent and a bioabsorbable polymer.

5. The method according to claim 4, wherein the frame is made of a biodegradable metal or a bioresorbable polymeric material.

6. The method according to claim 4, wherein the frame is made from material selected from a group consisting of magnesium alloy, polylactic acid, polycarbonate polymers, salicylic acid polymers or combination thereof.

7. The method according to claim 1, wherein the anesthetic agent is lidocaine or bupivacaine.

8. The method according to claim 1, wherein the prolonged period ranges from 3 to 6 months.

9. The method according to claim 1, wherein the sustained release device further comprises a coating on the frame and strands, wherein the coating comprises a base layer of a biocompatible material uniformly covering the frame and strands and one or more additional layers on the base layer, wherein the one or more additional layers comprise the anesthetic.

10. The method according to claim 9 wherein the biocompatible material is selected from a group consisting of poly(n-butyl methacrylate), poly(tetrafluoroethylene), poly(vinylidene fluoride-co-hexafluoropropylene), poly(styrene-b-isobutylene-b-styrene), Parylene C, poly(vinyl pyrrolidone), $TiO_2$, and a combination thereof.

* * * * *